(12) United States Patent
Vaillancourt et al.

(10) Patent No.: US 8,336,152 B2
(45) Date of Patent: Dec. 25, 2012

(54) INSERT FOR A MICROBIAL SCRUBBING DEVICE

(75) Inventors: Michael J. Vaillancourt, Chester, NJ (US); Marshall Kerr, Carlsbad, CA (US); Jeffrey D. Bright, Stansbury Park, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 183 days.

(21) Appl. No.: 12/860,114

(22) Filed: Aug. 20, 2010

(65) Prior Publication Data

US 2011/0030726 A1 Feb. 10, 2011

Related U.S. Application Data

(63) Continuation-in-part of application No. 11/732,075, filed on Apr. 2, 2007, now Pat. No. 8,065,773, and a continuation-in-part of application No. 12/752,744, filed on Apr. 1, 2010.

(60) Provisional application No. 61/274,739, filed on Aug. 20, 2009.

(51) Int. Cl.
*B08B 9/00* (2006.01)

(52) U.S. Cl. ............... 15/104.94; 15/104.93; 15/160

(58) Field of Classification Search ............... 15/104.04, 15/104.05, 104.92, 160, 104.93
See application file for complete search history.

(56) References Cited

U.S. PATENT DOCUMENTS

| | | |
|---|---|---|
| 2,878,128 A | 3/1959 | Jorgenson |
| 3,396,727 A | 8/1968 | Mount |
| 3,450,129 A | 6/1969 | Brewer |
| 3,860,348 A | 1/1975 | Doyle |
| 3,915,806 A | 10/1975 | Horlach |
| 3,961,629 A | 6/1976 | Richter et al. |
| 4,326,569 A | 4/1982 | Vaillancourt |
| 4,340,052 A | 7/1982 | Dennehey et al. |
| 4,354,490 A | 10/1982 | Rogers |
| 4,375,849 A | 3/1983 | Hanifl |

(Continued)

FOREIGN PATENT DOCUMENTS

CN 102448502 A 5/2012

(Continued)

OTHER PUBLICATIONS

JP 2008-094915 filed Apr. 1, 2008 Office Action dated Aug. 5, 2011.

(Continued)

*Primary Examiner* — Shay Karls
(74) *Attorney, Agent, or Firm* — Rutan & Tucker, LLP

(57) ABSTRACT

The microbial scrub brush in one embodiment employs an insert that is impregnated with an anti-bacterial disinfectant and that is housed within a housing of alcohol-compatible material and sealed over by a removable lid. The insert is maintained in sterile condition until ready for use. After removal of the lid, the insert is moved over the end of a female luer or other portion of a medical device and rotated in order to clean the exterior surface as well as the interior luminal surface of the device. In one embodiment, the insert includes a base from which extends an outer wall that defines a chamber. A plurality of complaint fingers extend from the base into the chamber. A plurality of wipers extend radially inward from the outer wall into the chamber to enable the cleansing of both the exterior surface and an interior surface of the medical device.

22 Claims, 6 Drawing Sheets

U.S. PATENT DOCUMENTS

| | | |
|---|---|---|
| 4,407,429 A | 10/1983 | Hekal |
| 4,417,890 A | 11/1983 | Dennehey et al. |
| 4,432,259 A | 2/1984 | Werth, Jr. |
| 4,432,764 A | 2/1984 | Lopez |
| 4,440,207 A | 4/1984 | Genatempo et al. |
| 4,453,636 A | 6/1984 | Meadows et al. |
| 4,465,200 A | 8/1984 | Percarpio |
| 4,484,595 A | 11/1984 | Vanek et al. |
| 4,513,888 A | 4/1985 | Curry |
| 4,551,146 A | 11/1985 | Rogers |
| 4,624,664 A | 11/1986 | Peluso et al. |
| 4,734,950 A | 4/1988 | Schenke et al. |
| 4,752,983 A | 6/1988 | Grieshaber |
| 4,778,447 A | 10/1988 | Velde et al. |
| 4,801,029 A | 1/1989 | Begley |
| 4,830,674 A | 5/1989 | Kaufman |
| 4,847,597 A | 7/1989 | Dobosi et al. |
| 4,862,549 A | 9/1989 | Criswell et al. |
| 4,867,309 A | 9/1989 | Germain |
| 4,872,135 A | 10/1989 | Peterson et al. |
| 4,872,235 A | 10/1989 | Nielsen |
| 4,886,388 A | 12/1989 | Gulker et al. |
| 4,893,956 A | 1/1990 | Wojcik et al. |
| 4,919,837 A | 4/1990 | Gluck |
| 4,981,230 A | 1/1991 | Marshall et al. |
| 4,989,733 A | 2/1991 | Patry |
| 5,049,139 A | 9/1991 | Gilchrist |
| 5,180,061 A | 1/1993 | Khan et al. |
| 5,193,525 A | 3/1993 | Silverstein et al. |
| 5,195,957 A | 3/1993 | Tollini |
| 5,203,771 A | 4/1993 | Melker et al. |
| 5,242,425 A | 9/1993 | White et al. |
| 5,274,874 A | 1/1994 | Cercone et al. |
| 5,308,406 A | 5/1994 | Wallock et al. |
| 5,330,235 A | 7/1994 | Wagner et al. |
| 5,332,113 A | 7/1994 | Kusler, III et al. |
| 5,368,049 A | 11/1994 | Raman et al. |
| 5,372,429 A | 12/1994 | Beaver, Jr. et al. |
| 5,382,297 A | 1/1995 | Valentine et al. |
| 5,471,706 A | 12/1995 | Wallock et al. |
| 5,531,341 A | 7/1996 | Shlisky |
| 5,536,258 A | 7/1996 | Folden |
| 5,554,135 A | 9/1996 | Menyhay |
| 5,566,823 A | 10/1996 | Summers |
| 5,613,521 A | 3/1997 | Knapp |
| 5,620,427 A | 4/1997 | Werschmidt et al. |
| 5,673,722 A | 10/1997 | Brass |
| 5,694,978 A | 12/1997 | Heilmann et al. |
| 5,719,113 A | 2/1998 | Fendler et al. |
| 5,722,537 A | 3/1998 | Sigler |
| 5,743,892 A | 4/1998 | Loh et al. |
| 5,763,412 A | 6/1998 | Khan et al. |
| 5,776,430 A | 7/1998 | Osborne et al. |
| 5,782,808 A | 7/1998 | Folden |
| 5,792,120 A | 8/1998 | Menyhay |
| 5,829,976 A | 11/1998 | Green |
| 5,830,488 A | 11/1998 | Suzuki et al. |
| 5,894,015 A | 4/1999 | Rechtin |
| 5,906,808 A | 5/1999 | Osborne et al. |
| 5,913,630 A | 6/1999 | Kelders et al. |
| 5,954,957 A | 9/1999 | Chin-Loy et al. |
| 5,980,925 A | 11/1999 | Jampani et al. |
| 6,000,580 A | 12/1999 | Nilson |
| 6,027,492 A | 2/2000 | Vetter |
| 6,045,539 A | 4/2000 | Menyhay |
| 6,045,623 A | 4/2000 | Cannon |
| 6,047,431 A | 4/2000 | Canonica |
| 6,086,275 A | 7/2000 | King |
| 6,096,701 A | 8/2000 | Mondin et al. |
| 6,108,847 A | 8/2000 | Cueman et al. |
| 6,110,292 A | 8/2000 | Jewett et al. |
| 6,116,468 A | 9/2000 | Nilson |
| 6,130,196 A | 10/2000 | Mondin et al. |
| 6,143,025 A | 11/2000 | Stobie et al. |
| 6,152,913 A | 11/2000 | Feith et al. |
| 6,245,056 B1 | 6/2001 | Walker et al. |
| 6,250,315 B1 | 6/2001 | Ernster |
| 6,254,550 B1 | 7/2001 | McNamara et al. |
| 6,289,547 B1 | 9/2001 | Narula et al. |
| 6,299,520 B1 | 10/2001 | Cheyne, III |
| 6,357,947 B1 | 3/2002 | Mark |
| 6,387,865 B1 | 5/2002 | Mondin et al. |
| 6,387,866 B1 | 5/2002 | Mondin et al. |
| 6,395,697 B1 | 5/2002 | Cheung et al. |
| 6,432,213 B2 | 8/2002 | Wang et al. |
| 6,447,446 B1 | 9/2002 | Smith et al. |
| 6,472,356 B2 | 10/2002 | Narula et al. |
| 6,488,942 B1 | 12/2002 | Ingemann |
| 6,508,601 B1 | 1/2003 | Lui et al. |
| 6,508,602 B1 | 1/2003 | Gruenbacher et al. |
| 6,564,415 B1 | 5/2003 | Katakura et al. |
| 6,589,212 B1 | 7/2003 | Navis |
| 6,617,294 B2 | 9/2003 | Narula et al. |
| 6,669,387 B2 | 12/2003 | Gruenbacher et al. |
| 6,699,233 B2 | 3/2004 | Slanda et al. |
| 6,708,363 B2 | 3/2004 | Larsen |
| 6,726,386 B1 | 4/2004 | Gruenbacher et al. |
| 6,745,425 B1 | 6/2004 | Tope |
| 6,821,043 B2 | 11/2004 | Teh |
| 6,824,015 B1 | 11/2004 | Ammann |
| 6,855,678 B2 | 2/2005 | Whiteley |
| 6,911,025 B2 | 6/2005 | Miyahara |
| 6,991,527 B2 | 1/2006 | Linzell |
| 7,021,848 B1 | 4/2006 | Gruenbacher et al. |
| 7,083,605 B2 | 8/2006 | Miyahara |
| 7,108,440 B1 | 9/2006 | Gruenbacher et al. |
| 7,144,172 B2 | 12/2006 | Zhadanov et al. |
| 7,163,914 B2 | 1/2007 | Gluck et al. |
| 7,179,007 B2 | 2/2007 | Wong et al. |
| 7,199,090 B2 | 4/2007 | Koivisto et al. |
| 7,282,177 B2 | 10/2007 | Castaneda |
| 7,282,186 B2 | 10/2007 | Lake, Jr. et al. |
| 7,338,927 B2 | 3/2008 | Shapiro |
| 7,347,458 B2 | 3/2008 | Rome et al. |
| 7,452,349 B2 | 11/2008 | Miyahara |
| 7,488,757 B2 | 2/2009 | Hoang et al. |
| 7,513,957 B2 | 4/2009 | Condliff |
| 7,537,779 B2 | 5/2009 | Modak et al. |
| D596,308 S | 7/2009 | Fisher |
| 7,560,422 B2 | 7/2009 | Shapiro |
| D607,325 S | 1/2010 | Rogers et al. |
| 7,682,561 B2 | 3/2010 | Davis et al. |
| 7,704,002 B2 | 4/2010 | Fisher et al. |
| 7,763,006 B2 | 7/2010 | Tennican |
| 7,794,675 B2 | 9/2010 | Lynn |
| 7,799,010 B2 | 9/2010 | Tennican |
| 7,828,777 B2 | 11/2010 | Vetter et al. |
| 7,834,328 B2 | 11/2010 | Redmond et al. |
| 7,857,793 B2 | 12/2010 | Raulerson et al. |
| 7,922,701 B2 | 4/2011 | Buchman |
| 7,931,877 B2 | 4/2011 | Steffens et al. |
| 7,972,322 B2 | 7/2011 | Tennican |
| 7,993,309 B2 | 8/2011 | Schweikert |
| 8,015,653 B2 | 9/2011 | Bargiel et al. |
| 8,065,773 B2 | 11/2011 | Vaillancourt et al. |
| 8,069,523 B2 | 12/2011 | Vaillancourt et al. |
| 2001/0031221 A1 | 10/2001 | Wu et al. |
| 2001/0031721 A1 | 10/2001 | Webb et al. |
| 2001/0032659 A1 | 10/2001 | Wang et al. |
| 2002/0002984 A1 | 1/2002 | Loy |
| 2002/0022660 A1 | 2/2002 | Jampani et al. |
| 2002/0062147 A1 | 5/2002 | Yang |
| 2003/0019767 A1 | 1/2003 | Cabrera |
| 2003/0144647 A1 | 7/2003 | Miyahara |
| 2003/0147925 A1 | 8/2003 | Sawan et al. |
| 2003/0156884 A1 | 8/2003 | Teh |
| 2003/0164175 A1 | 9/2003 | Linzell |
| 2003/0211066 A1 | 11/2003 | Scholz et al. |
| 2003/0213501 A1 | 11/2003 | Thomson et al. |
| 2003/0217423 A1* | 11/2003 | Larsen ..................... 15/104.92 |
| 2003/0233074 A1 | 12/2003 | Shields |
| 2004/0019990 A1 | 2/2004 | Farrell et al. |
| 2004/0052831 A1 | 3/2004 | Modak et al. |
| 2004/0111078 A1 | 6/2004 | Miyahara |
| 2004/0214785 A1 | 10/2004 | Dees et al. |
| 2004/0230162 A1 | 11/2004 | Tan |
| 2004/0237235 A1 | 12/2004 | Visioli et al. |

| | | |
|---|---|---|
| 2004/0258560 A1 | 12/2004 | Lake et al. |
| 2005/0081888 A1 | 4/2005 | Pung et al. |
| 2005/0124970 A1 | 6/2005 | Kunin et al. |
| 2005/0142945 A1 | 6/2005 | Mejlhede et al. |
| 2005/0147524 A1 | 7/2005 | Bousquet |
| 2005/0171489 A1 | 8/2005 | Weaver et al. |
| 2005/0177964 A1 | 8/2005 | Cisneros |
| 2005/0201812 A1 | 9/2005 | Wong et al. |
| 2005/0214185 A1 | 9/2005 | Castaneda |
| 2005/0215461 A1 | 9/2005 | Gluck et al. |
| 2005/0222542 A1 | 10/2005 | Burkholz et al. |
| 2005/0241088 A1 | 11/2005 | Brunner et al. |
| 2005/0241089 A1 | 11/2005 | Brunner et al. |
| 2005/0282727 A1 | 12/2005 | Shapiro |
| 2006/0003082 A1 | 1/2006 | Marumo et al. |
| 2006/0030827 A1* | 2/2006 | Raulerson et al. ............ 604/267 |
| 2006/0048313 A1 | 3/2006 | Yamaki |
| 2006/0102200 A1 | 5/2006 | Esquenet et al. |
| 2006/0189961 A1 | 8/2006 | Miyahara |
| 2006/0281663 A1 | 12/2006 | Asmus |
| 2007/0033753 A1 | 2/2007 | Kritzler |
| 2007/0065388 A1 | 3/2007 | Miyamoto et al. |
| 2007/0093762 A1 | 4/2007 | Utterberg et al. |
| 2007/0106205 A1 | 5/2007 | Connell et al. |
| 2007/0112333 A1 | 5/2007 | Hoang et al. |
| 2007/0130707 A1 | 6/2007 | Cohen et al. |
| 2007/0157408 A1 | 7/2007 | Bargiel et al. |
| 2007/0176117 A1 | 8/2007 | Redmond et al. |
| 2007/0225660 A1 | 9/2007 | Lynn |
| 2007/0266509 A1 | 11/2007 | Kohlruss et al. |
| 2007/0277852 A1 | 12/2007 | Condliff |
| 2007/0282280 A1 | 12/2007 | Tennican |
| 2008/0011310 A1 | 1/2008 | Anderson et al. |
| 2008/0014224 A1 | 1/2008 | Boyd et al. |
| 2008/0019889 A1 | 1/2008 | Rogers et al. |
| 2008/0033371 A1 | 2/2008 | Updegraff et al. |
| 2008/0034515 A1 | 2/2008 | Hilscher et al. |
| 2008/0038167 A1 | 2/2008 | Lynn |
| 2008/0039803 A1 | 2/2008 | Lynn |
| 2008/0086091 A1 | 4/2008 | Anderson et al. |
| 2008/0098543 A1 | 5/2008 | Esquenet et al. |
| 2008/0103210 A1 | 5/2008 | Shapiro |
| 2008/0132880 A1 | 6/2008 | Buchman |
| 2008/0137969 A1 | 6/2008 | Rueckert et al. |
| 2008/0138438 A1 | 6/2008 | Taylor et al. |
| 2008/0147047 A1 | 6/2008 | Davis et al. |
| 2008/0152894 A1 | 6/2008 | Beihoffer et al. |
| 2008/0155769 A1 | 7/2008 | Schonewille et al. |
| 2008/0172007 A1 | 7/2008 | Bousquet |
| 2008/0177250 A1 | 7/2008 | Howlett et al. |
| 2008/0187460 A1 | 8/2008 | Utterberg et al. |
| 2008/0194994 A1 | 8/2008 | Bown et al. |
| 2008/0235888 A1 | 10/2008 | Vaillancourt et al. |
| 2009/0008393 A1 | 1/2009 | Howlett et al. |
| 2009/0028750 A1 | 1/2009 | Ryan |
| 2009/0041619 A1 | 2/2009 | Cady et al. |
| 2009/0062766 A1 | 3/2009 | Howlett et al. |
| 2009/0099529 A1 | 4/2009 | Anderson et al. |
| 2009/0104281 A1 | 4/2009 | Taylor et al. |
| 2009/0117164 A1 | 5/2009 | Toreki et al. |
| 2009/0126134 A1 | 5/2009 | Whipple et al. |
| 2009/0137969 A1 | 5/2009 | Colantonio et al. |
| 2009/0143470 A1 | 6/2009 | Hoang et al. |
| 2009/0162301 A1 | 6/2009 | Tarrand |
| 2009/0165228 A1 | 7/2009 | Kilkenny et al. |
| 2009/0175759 A1 | 7/2009 | Davis et al. |
| 2009/0187148 A1 | 7/2009 | Knight |
| 2009/0191249 A1 | 7/2009 | Adelakun |
| 2009/0205151 A1 | 8/2009 | Fisher et al. |
| 2009/0226241 A1 | 9/2009 | McEwen et al. |
| 2009/0241991 A1 | 10/2009 | Vaillancourt et al. |
| 2009/0297400 A1 | 12/2009 | Cady et al. |
| 2010/0000040 A1 | 1/2010 | Shaw et al. |
| 2010/0047123 A1 | 2/2010 | Solomon et al. |
| 2010/0049170 A1 | 2/2010 | Solomon et al. |
| 2010/0050351 A1 | 3/2010 | Colantonio et al. |
| 2010/0083452 A1 | 4/2010 | Vaillancourt et al. |
| 2010/0200017 A1 | 8/2010 | Kerr et al. |
| 2010/0242993 A1 | 9/2010 | Hoang et al. |
| 2011/0030726 A1 | 2/2011 | Vaillancourt et al. |
| 2011/0039764 A1 | 2/2011 | Matsuno et al. |
| 2011/0039765 A1 | 2/2011 | Connor |
| 2011/0044850 A1 | 2/2011 | Solomon et al. |
| 2011/0046563 A1 | 2/2011 | Vetter et al. |
| 2011/0054440 A1 | 3/2011 | Lewis |
| 2011/0125104 A1 | 5/2011 | Lynn |
| 2011/0154591 A1 | 6/2011 | Ernster |
| 2011/0213339 A1 | 9/2011 | Bak |
| 2011/0213341 A1 | 9/2011 | Solomon et al. |
| 2011/0217212 A1 | 9/2011 | Solomon et al. |
| 2011/0265834 A1 | 11/2011 | Tennican |
| 2011/0284024 A1 | 11/2011 | Trebella et al. |
| 2011/0290799 A1 | 12/2011 | Anderson et al. |
| 2012/0000487 A1 | 1/2012 | Esquenet et al. |
| 2012/0016318 A1 | 1/2012 | Hoang et al. |

FOREIGN PATENT DOCUMENTS

| | | |
|---|---|---|
| DE | 10335794 A1 | 10/2005 |
| DE | 102005027982 A1 | 12/2006 |
| EP | 1977714 A1 | 10/2008 |
| JP | 60063051 A | 4/1985 |
| JP | 64017243 U | 1/1989 |
| JP | 2002301134 A | 10/2002 |
| JP | 2003319825 A | 11/2003 |
| JP | 2008094915 A | 4/2008 |
| JP | 2008253775 A | 10/2008 |
| WO | 9904623 A1 | 2/1999 |
| WO | 0015036 A1 | 3/2000 |
| WO | 2004018003 A1 | 3/2004 |
| WO | 2004084973 A2 | 10/2004 |
| WO | 2006019782 A2 | 2/2006 |
| WO | 2006062846 A2 | 6/2006 |
| WO | 2006138111 A1 | 12/2006 |
| WO | 2007084908 A2 | 7/2007 |
| WO | 2007097985 A2 | 8/2007 |
| WO | 2007137056 A2 | 11/2007 |
| WO | 2008100950 A2 | 8/2008 |
| WO | 2009123709 A2 | 10/2009 |
| WO | 2010039171 A1 | 4/2010 |
| WO | 2011022601 A1 | 2/2011 |

OTHER PUBLICATIONS

U.S. Appl. No. 12/079,965, filed Mar. 31, 2008 Final Office Action dated Aug. 31, 2011.
EP08250832 filed Mar. 12, 2008 EP Search Report dated Aug. 15, 2008.
PCT/US2009/002011 filed Mar. 30, 2009 Search Report dated Jun. 1, 2009.
PCT/US2009/002011 filed Mar. 30, 2009 Written Opinion dated Jun. 1, 2009.
PCT/US2009/005120 filed Sep. 14, 2009 Search Report dated Jul. 1, 2010.
PCT/US2010/029641 filed Apr. 1, 2010 Search Report dated Jul. 1, 2010.
PCT/US2010/029641 filed Apr. 1, 2010 Written Opinion dated Jul. 1, 2010.
U.S. Appl. No. 12/584,740, filed Sep. 11, 2009 Non-Final Office Action mailed Jul. 27, 2010.
U.S. Appl. No. 60/832,437, filed Jul. 21, 2006 entitled Disinfecting Cap.
U.S. Appl. No. 60/850,438, filed Oct. 10, 2006 entitled Disinfecting Cap.
U.S. Appl. No. 61/195,002, filed Oct. 2, 2008 entitled Site Scrub Brush.
U.S. Appl. No. 11/281,711, filed Nov. 17, 2005 Final Office Action dated Jun. 11, 2010.
U.S. Appl. No. 11/705,805, filed Feb. 12, 2007 Non-Final Office Action mailed Sep. 22, 2009.
U.S. Appl. No. 11/705,805, filed Feb. 12, 2007 Notice of Allowance mailed Jun. 21, 2010.
U.S. Appl. No. 11/732,075, filed Apr. 2, 2007 Non-Final Office Action dated Jul. 27, 2010.
U.S. Appl. No. 12/079,965, filed Mar. 31, 2008 Final Office Action dated Mar. 5, 2010.

U.S. Appl. No. 12/079,965, filed Mar. 31, 2008 Non-Final Office Action dated Oct. 2, 2009.
JP 2008-094915 filed Apr. 1, 2008 Office Action dated Jun. 1, 2012.
PCT/US11/37176 filed May 19, 2011 International Search Report dated Sep. 12, 2011.
PCT/US11/37176 filed May 19, 2011 Written Opinion dated Sep. 12, 2011.
PCT/US2009/002011 filed Mar. 30, 2009 International Preliminary Report on Patentability dated Oct. 5, 2010.
PCT/US2009/005120 filed Sep. 14, 2009 Preliminary Report on Patentability dated Apr. 5, 2011.
PCT/US2009/005120 filed Sep. 14, 2009 Written Opinion dated Jul. 1, 2010.
PCT/US2010/046096 filed Aug. 20, 2010 International Preliminary Report on Patentability dated Mar. 1, 2012.
PCT/US2010/046096 filed Aug. 20, 2010 Search Report dated Oct. 1, 2010.
PCT/US2010/046096 filed Aug. 20, 2010 Written Opinion dated Oct. 1, 2010.
U.S. Appl. No. 11/732,075, filed Apr. 2, 2007 Non-Final Office Action dated Jan. 4, 2011.
U.S. Appl. No. 11/732,075, filed Apr. 2, 2007 Notice of Allowance dated Apr. 14, 2011.
U.S. Appl. No. 12/079,965, filed Mar. 31, 2008 Final Office Action dated Jul. 6, 2012.
U.S. Appl. No. 12/079,965, filed Mar. 31, 2008 Non-Final Office Action dated Feb. 17, 2012.
U.S. Appl. No. 12/079,965, filed Mar. 31, 2008 Non-Final Office Action dated Mar. 9, 2011.
U.S. Appl. No. 12/584,740, filed Sep. 11, 2009 Final Office Action dated Feb. 17, 2011.
U.S. Appl. No. 12/584,740, filed Sep. 11, 2009 Notice of Allowance dated Jun. 21, 2011.
U.S. Appl. No. 12/752,744, filed Apr. 1, 2010 Non-Final Office Action dated May 3, 2012.

* cited by examiner

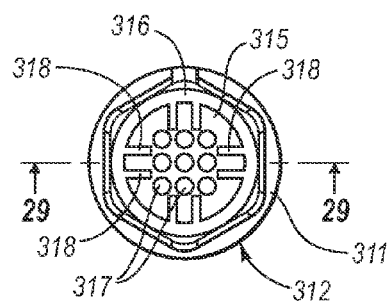
FIG. 28
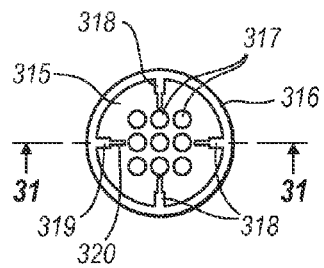
FIG. 30
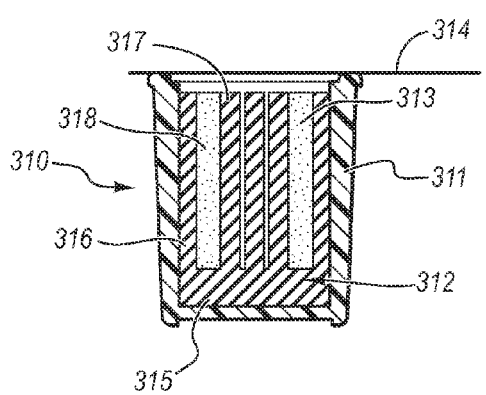
FIG. 29
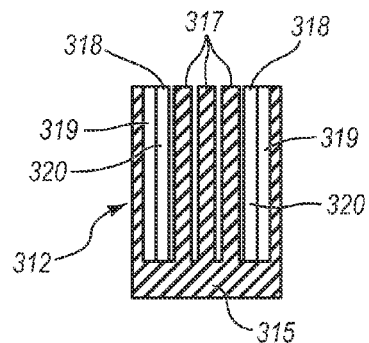
FIG. 31
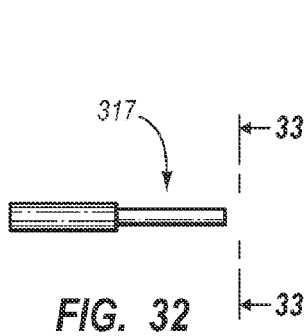
FIG. 32
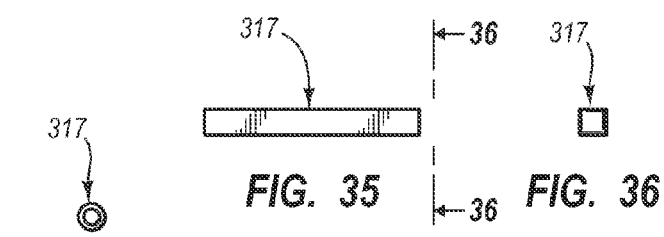
FIG. 35    FIG. 36
FIG. 33
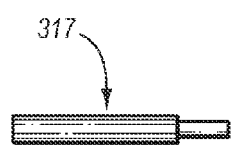
FIG. 34
FIG. 38    FIG. 37

INSERT FOR A MICROBIAL SCRUBBING DEVICE

CROSS-REFERENCE TO RELATED APPLICATIONS

This application claims the benefit of U.S. Provisional Patent Application No. 61/274,739, filed Aug. 20, 2009, and titled "Microbial Scrub Brush." This application is also a continuation-in-part of U.S. patent application Ser. No. 12/752,744 Publication No. 2010/0200017, filed Apr. 1, 2010, and titled "Microbial Scrubbing Device," which is a continuation-in-part of U.S. patent application Ser. No. 11/732,075 U.S. Pat. No. 8,065,773, filed Apr. 2, 2007, and titled "Microbial Scrub Brush." Each of these applications is incorporated herein by reference in its entirety.

BRIEF SUMMARY

Briefly, embodiments of the invention employ a swab in the form of a piece of foam material that is impregnated with an anti-bacterial disinfectant and into which a female luer or the like may be inserted for cleaning upon rotation of the piece of foam material about the luer.

In addition, the swab is disposed within a housing that allows a user to manipulate the swab using the fingers of a hand. In this respect, the swab is secured, for example, by an adhesive, within the housing so that after insertion of a female luer into the swab, the housing and, thus, the swab can be rotated by the user about the surfaces of the luer. The housing is also provided with indicia to indicate to the user the number of full turns of the housing about a luer when in use.

After securement of the swab in the housing, a removable lid is placed on the housing in order to maintain the sterility of the swab prior to use.

In particular, embodiments of the invention provide a microbial scrub brush that is comprised of a housing that defines a cavity, an insert of foam material that is disposed in the cavity and an anti-bacterial disinfectant in the insert.

The housing is sized to be readily handled using two or three fingers of a hand. Further, the housing is sized so that a female luer may be readily inserted into the insert within the housing cavity.

In one embodiment, the insert is provided with an annular portion for enveloping an outer surface of the female luer as well as a central portion for insertion within a central passage of the female luer for sterilizing an interior of the female luer.

The insert of foam material may be of any suitable material such as a semi-closed hydrophilic polyurethane medical grade foam. The foam material may also be a closed foam, an open foam or a semi-closed foam.

The anti-bacterial disinfectant may be of any suitable type and is in any suitable amount depending upon the size of the insert of foam material. For example, use is made of an aqueous solution containing about two percent (2%) chlorhexidine gluconate (chlorhexidine Solution) in an amount of from about 0.20 cc to about 0.75 cc, such as about 0.50 cc in one embodiment.

The scrub brush is also provided with a lid to seal the cavity and insert from the surrounding environment and to maintain the insert within the housing in a sterile condition and to keep the insert from drying out. The lid may also be provided with a pull tab to facilitate removal of the lid from the housing when the brush is to be used.

In normal operations, the lid is removed from the brush in order to expose the end of the insert within the housing. The brush is then placed over an exposed female luer, i.e., a needle-less connector, and rotated, for example for two complete revolutions. While rotating, the brush will self thread onto the female luer until the luer bottoms out. After completion, for example, of two full rotations, the brush can be removed from the luer by sliding the brush off the luer and discarded according to standard hospital protocol.

In one embodiment, the scrub brush includes an insert including a plurality of resilient fingers that substantially occupy a cross-sectional area of the cavity to enable the cleansing of both an exterior surface and an interior luminal surface of a medical device.

In another embodiment, the scrub brush insert includes a base from which extends an outer wall and a plurality of centrally disposed posts, or fingers. The insert can further include a plurality of wipers that extend radially inward from the outer wall. The fingers are configured to cleanse an interior portion of a medical device that is inserted into the cavity of the scrub brush, while the wipers of the outer wall are configured to cleanse exterior portions of the device when the scrub brush is rotated thereabout. The scrub brush insert in one embodiment is injection molded from silicone, though other materials and forming processed can also be employed.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 28 illustrates a top view of a scrub brush with a lid removed in accordance with one embodiment;

FIG. 29 illustrates a cross-sectional view of the scrub brush of FIG. 1 taken on the line 29-29 of FIG. 28 with a lid in place;

FIG. 30 illustrates a top view of a modified insert in accordance with one embodiment;

FIG. 31 illustrates a cross-sectional view of the scrub brush of FIG. 30 taken on the line 31-31 of FIG. 30;

FIG. 32 illustrates a side view of a finger of stepped profile for an insert in accordance with one embodiment;

FIG. 33 illustrates an end view of the finger of FIG. 32 taken on the line 33-33 of FIG. 32;

FIG. 34 illustrates a side view of a modified finger of stepped profile for an insert in accordance with one embodiment;

FIG. 35 illustrates a side view of a finger of uniform profile for an insert in accordance with one embodiment;

FIG. 36 illustrates an end view of the finger of FIG. 35 showing a square cross-section;

FIG. 37 illustrates an end view of the finger of uniform profile with a round cross-section; and FIG. 38 illustrates an end view of the finger of uniform profile with a triangular cross-section.

DETAILED DESCRIPTION OF SELECTED EMBODIMENTS

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Figure 1:
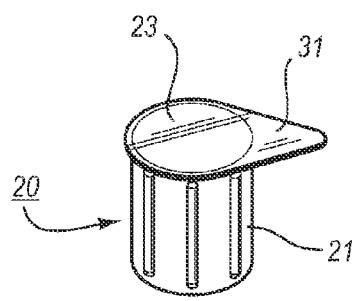
FIG. 1 illustrates a perspective view of a microbial scrub brush in accordance with one embodiment.
Figure 2:
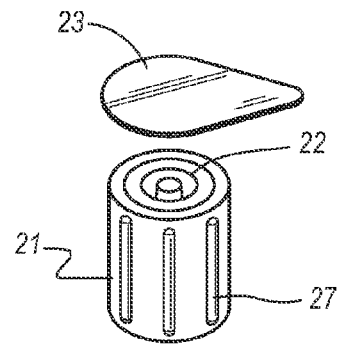
FIG. 2 illustrates an exploded view of the scrub brush of FIG. 1.

Referring to FIGS. 1 and 2, the microbial scrub brush 20 is comprised of a housing 21, a swab in the form of an insert 22 and a lid 23.

Figure 3:
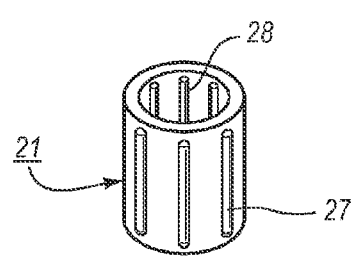
FIG. 3 illustrates a perspective view of the housing of the scrub brush of FIG. 2.
Figure 4:
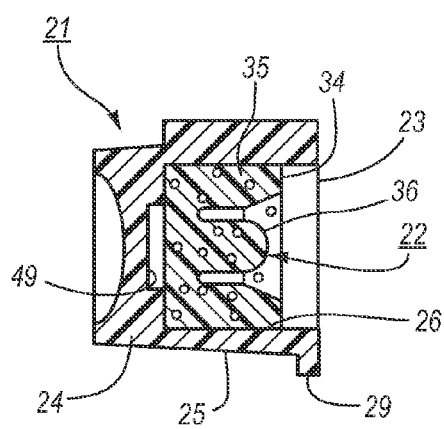
FIG. 4 illustrates a cross-sectional view of the scrub brush of FIG. 1.

Referring to FIGS. 3 and 4, the housing 21 is of one piece in a cup shape and is formed of a base 24 and a ring 25 integral with the base 24 to define a cavity 26 of cylindrical shape with an open end. The housing 21 is made by injection molding and is made of an alcohol compatible material, such as polypropylene or polyethylene, for instance.

As indicated in FIG. 4, the cavity 26 is coaxial of the longitudinal axis of the housing 21. The overall dimensions of the housing 21 are such that the housing 21 may be readily handled and rotated using two or three fingers of a hand. For example, the housing 21 may have an outside diameter of 0.725 inches and a length of 0.650 inches. In another embodiment, the housing includes an outside diameter of about 0.75 inches and a length of about 0.90 inches. Of course, other housing dimensions are possible, in accordance with the nature of intended use.

Referring to FIG. 3, the housing 21 has a plurality of ribs 27 of the exterior surface of the ring 25 to provide a gripping surface. Any other suitable type of knurling may also be used. The housing 21 may also contain a plurality of ribs 28 on the interior surface of the ring 25 that extend into the cavity 26 in order to engage the insert 22 (not shown) to prevent the insert 22 from rotating within the cavity 17. Optionally, the insert 22 may be adhesively secured against rotation within the housing 21.

Referring to FIG. 4, the housing 21 is provided with an indicia, for example in a form of a projecting index bar 29, on the exterior surface in order to indicate a degree of rotation of the housing 21 when in use and, particularly, the number of rotations that the brush 20 is turned during use.

Figure 5:
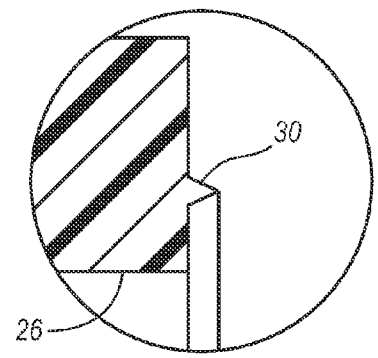
FIG. 5 illustrates a detailed view of a surface of the housing of FIG. 4.

Referring to FIG. 5, the housing 21 has an annular boss 30 at one end concentric to the cavity 26 for heat sealing of the lid 23 thereon. In this respect, the lid 23 is a die-cut foil lid that is coated with a material that readily heat seals to the polypropylene housing 21 via the boss 30. As indicated in FIG. 1, the lid 23 is provided with a pull tab 31 that extends therefrom and from the housing 21 in order to facilitate manual removal of the lid 23 from the housing 21.

Figure 6:
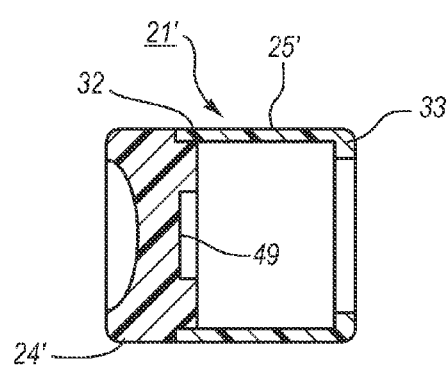
FIG. 6 illustrates a cross-sectional view of a modified housing in accordance with one embodiment.

Referring to FIG. 6, wherein like reference characters indicate like parts as above, the housing 21' may also be made in a two-piece construction. For example, the housing 21' includes a base 24' that receives a ring 25' in a fixed relation. As indicated, the base 24' has a shouldered annular portion 32 that receives the ring 25' in a recessed manner so that a smooth outer surface is presented by the base 24' and ring 25'.

In addition, the ring 25' is provided with an inwardly directed lip 33 at an end opposite the base 24' in order to retain an insert 22 (not shown) therein.

Figure 7:
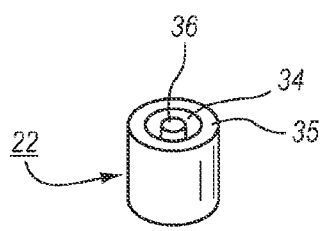
FIG. 7 illustrates a perspective view of the insert of the scrub brush of FIG. 2.

Referring to FIGS. 4 and 7, the insert 22 is a foam material, for example, of injection molded construction or the insert 22 may be die-cut from a foam sheet. The insert 22 is mounted in the housing 21 to be exposed to the open end of the housing 21.

The distal end 34 of the insert 22 is flat and slightly recessed within the open end of the housing 21 and the proximal end of the insert 22 is flat and can be secured by way of a suitable adhesive onto the base 24 of the housing 21. Typically, the insert 22 has an outer diameter of 9/16 inch (0.5625 inches).

The insert 22 includes an annular portion 35 and a central portion 36 with a flat end within the annular portion 35. The flat end of the central portion 36 may be co-planar with the end of the annular portion 35 as indicated in FIG. 7 or may be recessed within the annular portion 35 as indicated in FIGS. 4 and 8.

Figures 8, 9:
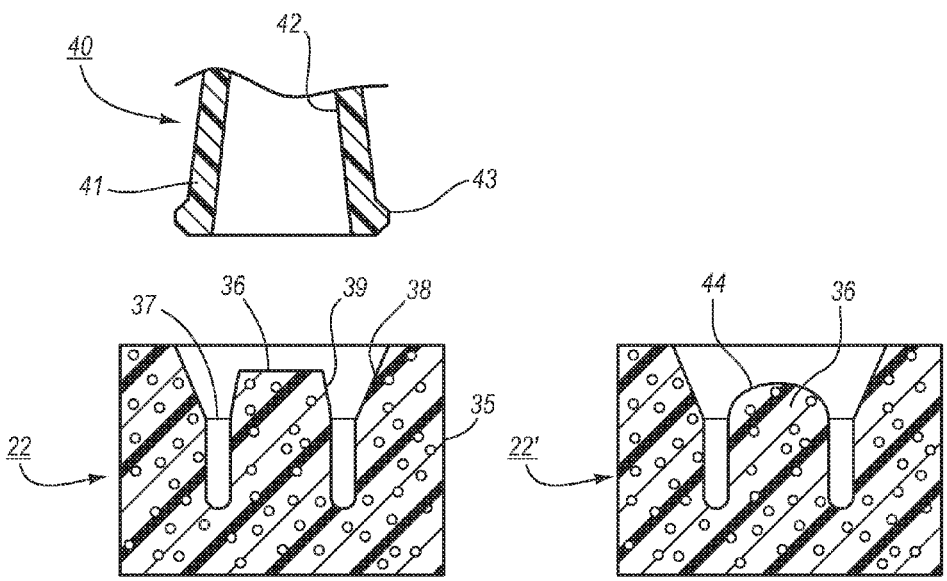
FIG. 8 illustrates a view of a female luer being inserted into the insert of the scrub brush in accordance with one embodiment.
FIG. 9 illustrates a cross-sectional view of a modified insert in accordance with one embodiment.

As illustrated in FIG. 8, the insert two portions 35, 36 are circumferentially spaced apart to define an annular gap 37 therebetween. In addition, the annular portion 35 has a conical inwardly directed surface 38 that provides a narrowing entrance to the gap 37 for a female luer 40 while the central portion 36 has an outer conical surface 39 that is formed with a 6% taper for engagement with the taper of the female luer 40.

The exterior of the insert 22 may be formed to match and interlock with the internal ribs 28 of the housing 21 (see FIG. 3) to prevent rotation of the insert 22 within the housing 21.

The insert 22 is made of a semi-closed cell, hydrophilic polyurethane medical grade foam with a moderate absorption rate. The foam configuration and size is such as to hold 0.5 cc of an anti-bacterial solution with no solution leak-out.

During assembly of the scrub brush 20, the insert 22 is first secured within the housing 21 and then impregnated with the anti-bacterial solution. Thereafter, the lid 23 is secured to the housing 21.

Referring to FIG. 8, the insert 22 is sized to be used with a female luer 40 having an outer peripheral surface 41, a central passage 42 and a flange 43 about the passage 42. As indicated, the annular portion 35 of the insert 22 is sized to envelope and wipe the outer surface 41 of the female luer 40 and the central portion 36 is sized to move into the passage 42 of the female luer 40 for wiping the passage 42.

In normal operation, the lid 23 is removed to expose the insert 22 and the brush 20 is placed over the female luer 40 with the luer 40 inserted into the gap 37 between the two portions 35, 36 of the insert 22. The conical entrance portion 38 of the insert 22 facilitates centering of the brush 20 on the luer 40.

Next, the brush 20 is rotated. The rotation of the brush 20 causes a self-threading of the insert 22 into the passage 42 of the luer 40 until the luer 40 bottoms at the base of the gap 37 defined by the annular portion 35 and the central portion 36 of the insert 22. Typically, the brush 20 is rotated 360 degrees twice. Upon completion of two full rotations, the brush 20 can be removed by sliding the brush 20 off the luer 40 and discarded.

The housing 21 of the scrub brush 20, when sealed by the lid 23, protects against drying out of the insert 22 and after removal of the lid 23 serves as a convenient holder for wiping of the insert 22 about a female luer or the like.

Referring to FIG. 9, wherein like reference characters indicate like parts as above, the central portion 36 of the insert 22' may be provided with a rounded end or crown 44 rather than a flat surface as indicated in FIG. 8. The rounded crown 44 is particularly useful where the scrub brush 20 is used to clean a swabable luer having a flat end or the like (not shown). In this case, the peak of the crown 44 would first contact the flat end of the swabable luer in a point-to-point manner. Then, as the brush 20 is further pushed against the luer, the crown 44 would compress thereby compressing the central portion 36 of the insert 22'. As the brush is then rotated, a scrubbing action takes place between the surface of the now compressed central portion 36 and the luer surface.

Figures 10, 11:
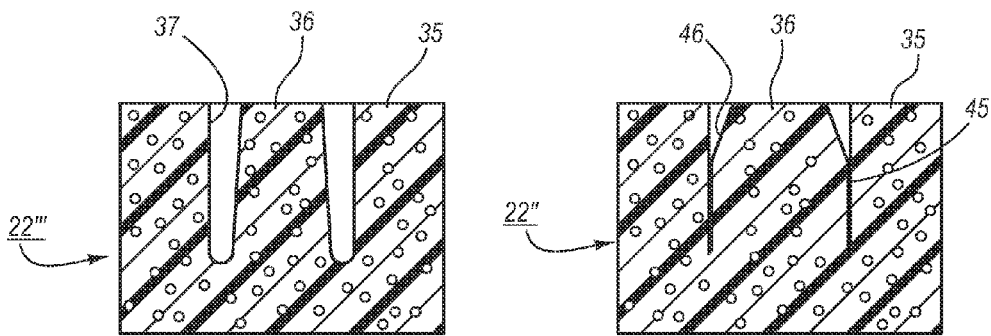
FIG. 10 illustrates a cross-sectional view of a further modified insert in accordance with one embodiment.
FIG. 11 illustrates a cross-sectional view of a further modified insert in accordance with one embodiment.

Referring to FIG. 10, wherein like reference characters indicate like parts as above, the insert 22" may be constructed without a gap between the annular portion 35 and central portion 36. In this embodiment, the two portions 35, 36 are contiguous to each other and define a slit 45 rather than a gap for receiving a luer. Further, the central portion 36 is co-extensive with the annular portion 35, i.e., the central portion 36 is not recessed, and is provided with a conically tapered surface 46 at the entrance end to the slit 45 to provide a small gap with the annular portion 35.

Referring to FIG. 11, wherein like reference characters indicate like parts as above, the insert 22''' may be constructed with an annular gap 37 between the annular portion 35 and central portion 36 that extends for the full depth of the central portion 36 without a conical entrance portion as in FIG. 8.

Figure 12:
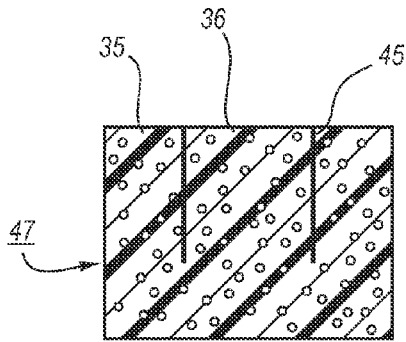
FIG. 12 illustrates a cross-sectional view of an insert that is die cut in accordance with one embodiment.
Figure 13:
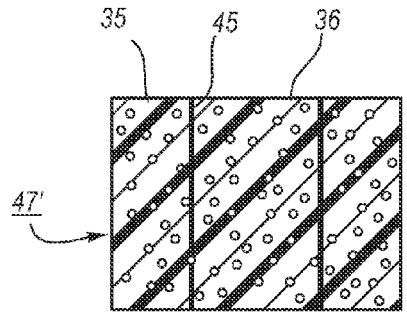
FIG. 13 illustrates a cross-sectional view of a modified die-cut insert in accordance with one embodiment.
Figure 14:
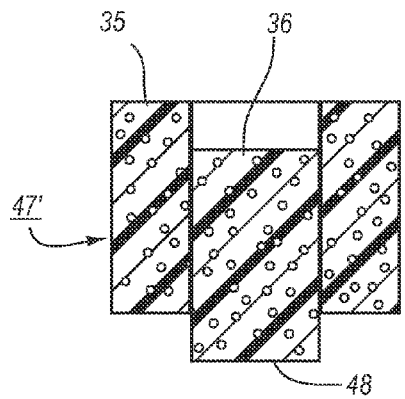
FIG. 14 illustrates a cross-sectional view of a further modified die-cut insert in accordance with one embodiment.

Referring to FIG. 12, wherein like reference characters indicate like parts as above, the insert 47 is die cut to form a slit 45 with the two portions 35, 36 contiguous to each other. As illustrated, the slit 45 extends from the face of the insert 47 and terminates short of the rear end of the insert 47. Alternatively, the slit 45 may extend completely through the insert 47' as shown in FIG. 13. Also, the central portion 36 may be pushed relative to the annular portion 35 so as to extend beyond the annular portion 36 as shown in FIG. 14. In this latter case, the exposed rear end 48 of the central portion 36 may extend into a recess 49 formed in the base 24 of the housing 21 (see FIG. 4) and be secured therein by an adhesive.

Figure 15:
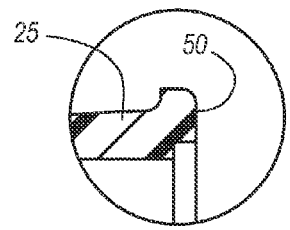
FIG. 15 illustrates a modified surface on the housing for receiving a closure lid.

Referring to FIG. 15, wherein like reference characters indicate like parts as above, the housing ring 25 may be formed with a flat surface 50 that is textured in order to receive an adhesive for securing the lid 23 (see FIG. 4) in place or the lid 23 may be heat sealed in place.

Figure 17:
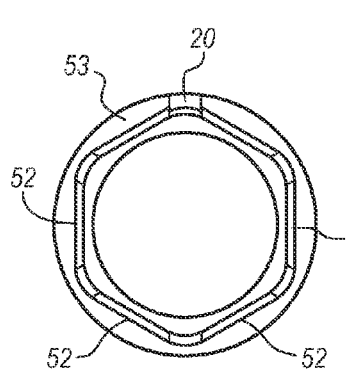
FIG. 17 illustrates a rear closed end view of the housing of FIG. 16.
Figure 16:
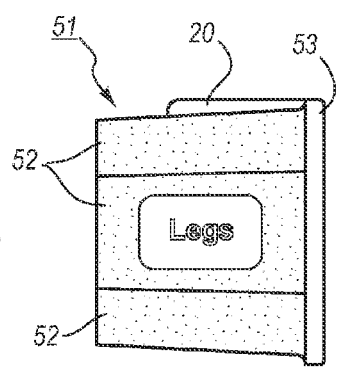
FIG. 16 illustrates a side view of a modified housing in accordance with one embodiment.
Figure 18:
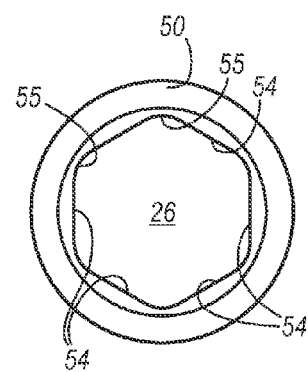
FIG. 18 illustrates a front open end view of the housing of FIG. 16.

Referring to FIGS. 16 to 18, wherein like reference characters indicate like parts as above, the housing 51 may be made with a polygonal outer cross-section, such as a hexagonal cross-section, to provide a plurality of contiguous flat surfaces 52 for easier gripping by the fingers of a user's hand. These surfaces 52 may be textured or roughened to facilitate gripping. Also, one or more of the flat surfaces may be provided with indicia, such as a logo of the manufacturer or the like.

The housing 51 has a short flange 53 at the open end that is also provided to form a surface 50 for receiving a lid 23 as described above.

In addition, the housing 51 has a cavity 26 that is of a polygonal shape complementary to the outer cross-section to provide a plurality of flat walls 54. The cavity 26 and walls 54 are sized to receive the insert 22 in a compressed condition. That is, for a cylindrical insert 22 of 9/16 inch diameter, the oppositely disposed walls 54 are spaced apart by 0.500 inches and the oppositely disposed corners 55 formed by the walls 54 are spaced apart 0.553 inches. The insert 22 is, thus, circumferentially compressed within the cavity 26.

When a luer is inserted into the insert 22 in the housing 51, the degree of compression imposed upon the insert 22 when placed in the housing 51 causes the insert to wipe the surfaces of the luer with a scrubbing action.

The scrub brush 20 may be modified in various manners. For example, where the device being cleaned does not have a central passage, the insert 22 of the scrub brush 20 may be made without a central portion 36. In this embodiment, the scrub brush would be placed over the end of the device and then rotated so as to thread the scrub brush onto the end of the device for disinfecting purposes. Also, in this embodiment, having the insert mounted in the housing in a circumferentially compressed manner would facilitate the disinfecting action of the scrub brush on the device.

Embodiments of the invention thus provide a device that is easily handled and that is able to disinfect a female luer in an easy manner. Further, embodiments of the invention provide a device that is able to disinfect the interior of a female luer. This is a particular advantage over a cloth type wipe that cannot be readily inserted into the passage of a female luer.

Embodiments of the invention further provide an insert that is impregnated with an anti-bacterial solution for decontamination of a luer site that is contained in a sterile condition until ready for use and that can be readily manipulated when in use.

FIGS. 19-27 depict further details regarding a microbial scrubbing device in accordance with embodiments of the present invention. As many of the features described above may be included in the scrubbing devices to be discussed below, only selected features are included in the following discussion. As such, the following discussion should not be intended to limit the scope of the embodiments described herein.

Figure 19:
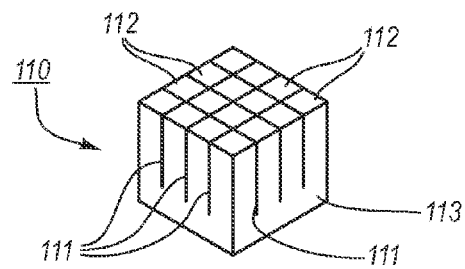
FIG. 19 illustrates a perspective view of a foamed plastic insert in accordance with one embodiment.

Referring to FIG. 19, the foamed plastic insert 110 includes a cubic shape. In addition, the insert 110 is digitated, i.e., is cross-cut with slits 111 in each of two perpendicular directions to form separate parallel fingers 112 of rectangular cross-sectional shape. The slits 111 extend downwardly a major fraction of the height of the insert 110, e.g., about ¾ of the height of the insert 110 so that the fingers 112 extend integrally and upwardly from a common base 113 of rectangular cross-sectional shape. As illustrated, the slits 111 are spaced apart to define a 4-by-4 grid of fingers 112.

In one embodiment, the foam insert 110 includes a length of ⅝ inch, a width of ⅝ inch and a height of ¾ inch. Note, however, that the length of the fingers as well as the size and shape of the foamed insert can vary from what is explicitly described herein. For instance, instead of including a square cross-sectional shape, the fingers in one embodiment can include a triangular, round or other polygonal shape, as seen further below.

Note that in one embodiment the insert 110 includes a semi-closed cell, hydrophilic polyurethane medical grade foam in the present embodiment. In another embodiment, the insert 110 includes a low density, closed cell polyethylene foam. It is appreciated that the insert 110 in other embodiments can include other suitable materials. Characteristics of a suitable material include sufficient deformability, ability to retain a cleansing substance such as an antibacterial solution, suitable resistance to tearing or separation, and stability in the presence of the cleansing substance. In one embodiment, a closed cell material including sufficient surface tension to suspend the cleansing substance on the surface of the fingers can be employed.

In other embodiments, Generally, various other materials can be employed to form the insert. Examples of these include low durometer, medical grade elastomers and foams that exhibit the desired characteristics described above. Further non-limiting examples include polyurethane including closed/semi-closed/open cell polyurethane foam, silicone including silicone rubber and closed/semi-closed/open cell silicone foam, polyethylene, polypropylene, and a thermoplastic elastomer including rubber and polypropylene sold under the name SANTOPRENE.

Further, in one embodiment it is appreciated that the insert can include two or more materials included together to provide different regions with differing scrubbing characteristics, e.g., differing abrasive characteristics. These and other modifications to the insert are therefore contemplated.

Figure 20A:
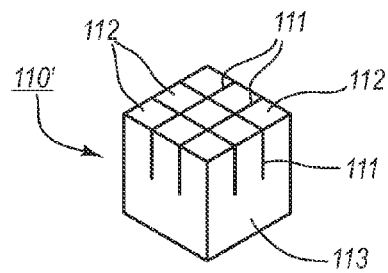
FIG. 20A illustrates a perspective view of a foamed plastic insert in accordance with one embodiment.
Figure 20B:
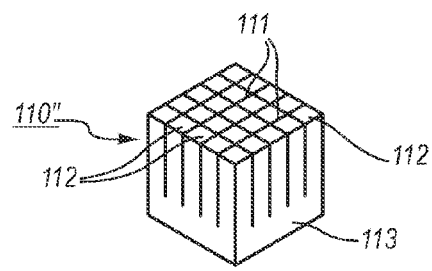
FIG. 20B illustrates a perspective view of a foamed plastic insert in accordance with one embodiment.

Referring to FIGS. 20A and 20B, wherein like reference characters indicate like parts as above, the foamed insert may have slits 111 that define a different number of fingers 112, i.e., a 3-by-3 grid of fingers 112 in the insert 110', or a 5-by-5 grid of fingers 112 in the insert 110". Any suitable number of fingers 112 may be formed in an insert 110 with the spacing of the slits 111 being adapted to the number and/or size of the fingers 112 desired for the insert 110 and the use to which the insert 110 is to be subjected. It is further appreciated that the shape and size of the insert can vary according to shape, size, and number of fingers included therewith.

Figure 21:
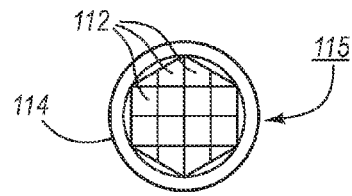
FIG. 21 illustrates a top view of the insert of FIG. 19 in a holder of circular cross-sectional shape to form a scrub brush in accordance with one embodiment.

Referring to FIG. 21, wherein like reference characters indicate like parts as above, the insert 110 is placed in a holder 114 of hexagonal cross-sectional shape to form a scrub brush 115 similar to the scrub brush described in previous embodiments further above. The holder 114 is sized with the opposite interior walls (flats) spaced ½ inch apart so that the insert 110 is compressed, particularly at the corners, when fitted into the cavity of the holder 114 as indicated in FIG. 21. A suitable hot melt glue or other suitable adhesive may be used to adhere the insert 110 to the bottom of the holder 114. Of course, other suitable methods can be employed to secure the insert 110 to the holder 114, including mechanical fixation for instance. In one embodiment, the compression provided by the holder once the insert is inserted therein is sufficient to maintain the insert in position within the holder.

Figure 22:
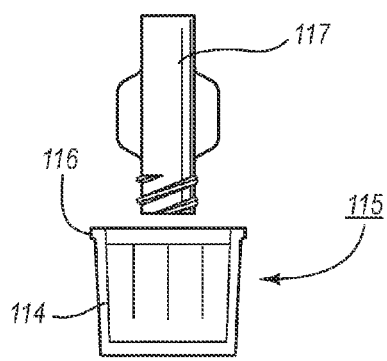
FIG. 22 illustrates a view of an externally threaded catheter in a position to be inserted and turned within the scrub brush of FIG. 21.

As indicated in FIG. 22, the cavity of the holder 114 includes a depth suitable to receive the insert 110 in a recessed manner. So disposed within the holder 114, the insert 110 in the present embodiment substantially fills the cavity of the holder. In other embodiments, the insert can be sized so as to fill the holder cavity to depths different from that shown here.

The insert 110, when disposed in the cavity of the holder 114, substantially occupies a cross-sectional area of the cavity, as best seen in FIG. 21. This enables the fingers to be disposed across a cross-sectional area sufficient to clean both exterior and interior surfaces of a portion of a medical device inserted into the holder 114. It is appreciated that the holder and the cavity it defines can assume other shapes, including square, round, etc. Indeed, the holder, its cavity, and the insert disposed therein can be configured in shape and size so as to enable the scrub brush 115, as a scrubbing device, to cleanse a particular size and configuration of a medical device.

As in previous embodiments a cleansing substance, such as a solution of a suitable microbialcide or germicide, is impregnated into the insert 110 while in the holder 114. The cleansing substance can include an anti-bacterial disinfectant of any suitable type and suitable amount depending upon the size of the insert of foam material. For example, in one embodiment use is made of an aqueous solution including about two percent (2%) chlorhexidine gluconate (chlorhexidine solution, "CHG") by volume in an amount of from about 0.20 cc to about 0.75 cc. Optionally, a solution including about 0.50 cc is employed. In another embodiment, a solution including about 70 percent (70%) isopropyl alcohol ("IPA") in an aqueous solution is included in the cleansing substance. In yet another embodiment, a solution including about 70 percent (70%) IPA and about two percent (2%) CHG in an aqueous solution in an amount of about 0.2 ml is included in the cleansing substance. In the latter solution, it is recognized that the concentration of IPA can vary from about 60 percent (60%) to about 90 percent (90%) and the concentration of CHG can vary from about one percent (1%) to about five percent (5%), in one embodiment.

Other suitable solution compositions and concentrations are also possible. For instance, povidone iodine or hydrogen peroxide solutions can be included in the cleansing substance, in one embodiment.

In the case where it is a liquid, desired characteristics for the cleansing substance include a solution including suitable surface tension so as to be retained by the fingers and enable cleansing contact with the medical device portion to be cleansed.

Figure 23:
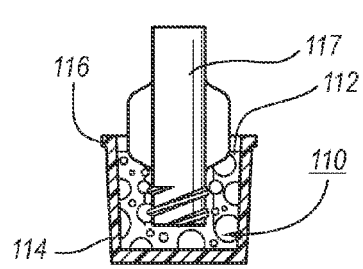
FIG. 23 illustrates a cross-sectional view of the scrub brush of FIG. 21 during rotation of the externally threaded catheter of FIG. 22 therein.

Referring to FIG. 23, wherein like reference characters indicate like parts as above, the holder 114 includes an annular lip 116 around the tip edge to define a land for receiving a sealing membrane (not shown) that seals the interior of the holder 114 and the solution-impregnated insert 110 therein against contamination from the outside environment until the scrub brush 115 is to be used.

Note that, in one embodiment, the scrub brush 115 may be provided with the cleansing substance, including a microbialcide or germicide for instance, at the point and time of use by injecting or otherwise introducing the cleansing substance or germicide after the sealing membrane has been removed from the holder 114.

In one embodiment, use of the scrub brush 115 as a scrubbing device proceeds as follows: after removal of the sealing membrane by a user, the object to be cleaned, e.g., a portion of an externally threaded hollow catheter 117, or a female type luer connector, is inserted by the user into the foamed insert 110. At this time, as indicated in FIG. 23, the fingers 112 of the insert 110 directly under the surfaces of the inserted portion of the catheter 117 are depressed into the holder 114, the fingers located outside the periphery of the catheter remain upright and lay against the outer peripheral surface of the catheter portion, and the fingers located directly under the lumen (bore) of the catheter pass into the lumen. The separate reactions of the fingers 112 are facilitated by the fingers 112 being formed in a digitated manner to be separated from each other as described above.

Once the portion of the catheter 117 has been inserted into the foamed insert 110 of the scrub brush 115, the holder 114 is rotated relative to the catheter portion. For example, the user may hold the catheter 117 stationary while rotating the scrub brush 115 or vice versa. In either case, the scrub brush 115 is rotated a sufficient number of times relative to the catheter 117 to sufficiently kill any bacteria the solution-impregnated foam insert 110 comes in contact with and/or to remove any biofilm from the outside peripheral surface and external thread as well as the inside surface of the lumen (bore) of the catheter 117, for example as described in U.S. patent application Ser. No. 12/079,965, filed Mar. 31, 2008, which application is incorporated herein by reference in its entirety. In this way, both exterior surfaces and interior luminal surfaces of the portion of the catheter 117 are scrubbed by the respective fingers 112 of the insert 110, causing the cleansing substance carried by the fingers to disinfect the surfaces and remove any biofilm disposed thereon. Note that in one embodiment, a series of from about six to about ten rotations of the scrub brush 115 relative to the catheter 117 is suitable for cleansing the aforementioned surfaces. In other embodiments, other numbers of rotations are possible. In yet another embodiment, a back-and-forth twisting motion is employed to scrub the fingers against the medical device portion being cleansed. In the latter case, a series of eight back-and-forth twists is employed, according to one embodiment, though other numbers of twists or uni-directional/multi-directional motions are, of course, possible.

Figure 24:
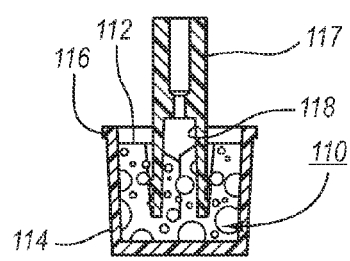
FIG. 24 illustrates a cross-sectional view of an externally threaded catheter and scrub brush at a point during rotation of the catheter in the foamed insert of the scrub brush.

Referring to FIG. 24, wherein like reference characters indicate like parts as above, when the catheter 117 is inserted into the foamed insert 110, the fingers 112 that pass into a lumen 118 of the catheter 117 are slightly compressed due in part to the frictional forces between the interior luminal wall of the lumen 118 and the fingers 112 in contact therewith. The degree of compression is such as to enhance the degree of contact between the fingers 112 and the luminal wall of the lumen 118 and thus enhance the scrubbing action of the fingers 112 on the luminal wall. It is appreciated that the same scrubbing enhancement is realized on fingers in contact with exterior portions of the catheter 117 and other suitable portions of medical devices cleansed by the scrub brush, including a female-type luer connector, for instance.

As indicated in FIG. 24, the medical device, such as a male or female luer, standard or needleless connector, or other object to be inserted in the scrub brush 115, may have any suitable peripheral shape or contour for its exterior surface, as well as any suitable interior luminal surface or lumen 118. The lumen 118 may be of conically tapered shape, as illustrated, or may be of uniform diameter. In another embodiment, no interior luminal surface is included.

Figure 25:
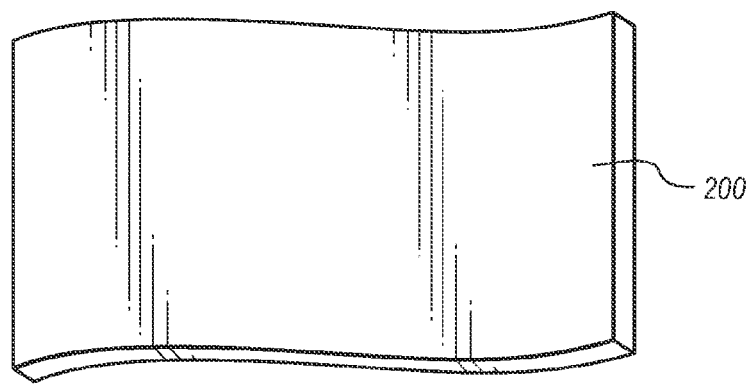
FIG. 25 illustrates a perspective view of a sheet of material for use in a scrub brush in accordance with one embodiment.
Figure 26:
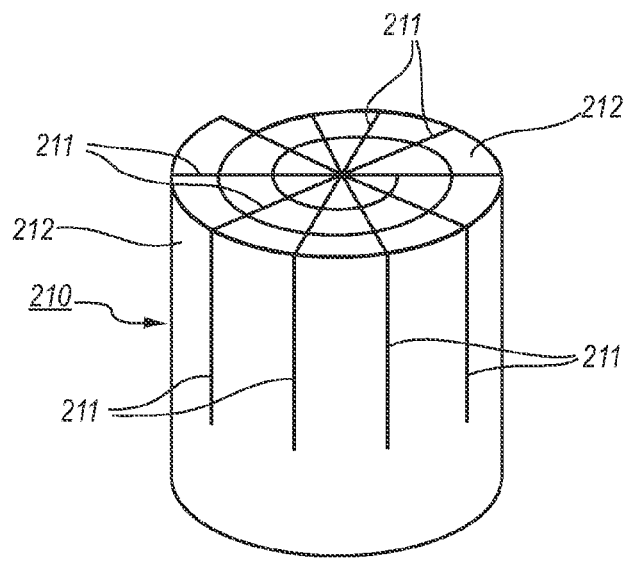
FIG. 26 illustrates a perspective view of the sheet of FIG. 25 in a rolled-up and slit configuration to define an insert of the scrub brush.
Figure 27:
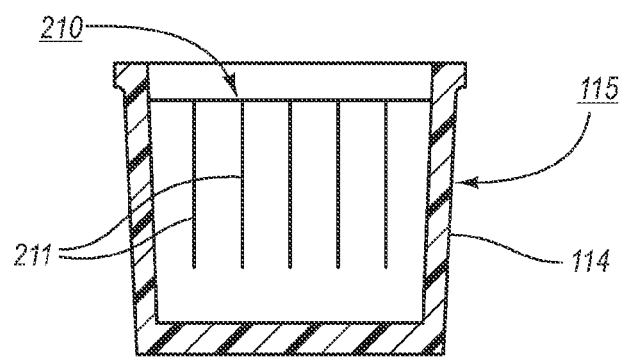
FIG. 27 illustrates a cross-sectional side view of a holder of a scrub brush including the rolled up and slit sheet of FIG. 26 disposed in a cavity of the holder, according to one embodiment.

FIGS. 25-27 depict various details regarding a scrubbing device including an insert configured according to one embodiment. In particular, a sheet 200 of suitable material shown in FIG. 25 is rolled into a rolled-up configuration, as shown in FIG. 26, to define an insert 210. A plurality of slits 211 is cut into the rolled sheet 200 a predetermined distance to define a plurality of fingers 212. As shown in FIG. 27, the rolled-up insert 210 can be inserted into the cavity of the holder 114 of the scrub brush 115, with a suitable cleansing substance added thereto.

The sheet 200 can include any one of a variety of suitable materials, including polyurethane foam, polyethylene foam, polyester, or other suitable natural or synthetic materials. Further, the material defining the sheet 200 can include a homogeneous, woven, knit, fibrous, or non-woven configuration, among others. In the case of fibrous materials, the fibers of the material are aligned parallel with the slits in one embodiment in order to impart suitable tear resistance to the fingers.

FIGS. 28 and 29 depict a scrub brush 310 according to one embodiment, including a hexagonally shaped holder 311, similar to previous embodiments. A swab, or insert 312, includes a generally cylindrical body with a flat base 315 and an outer cylindrical wall 316 extending therefrom. The wall 316 of the insert 312 defines a chamber in which are disposed a plurality of centrally disposed fingers 317 extending upwardly from the insert base 315, best seen in FIG. 29. In addition, a plurality of wipers 318 extend radially inward into the chamber from the insert wall 316. The insert 312 can be secured to the interior of the holder 311 via an adhesive to bind the insert base to the bottom of the holder cavity, or via another suitable fixation. In another embodiment, the holder and cleansing insert are integrally formed as a single unit.

In one embodiment, the insert 312 includes silicone, such as a medical grade silicone rubber, or from another suitable material as described further above. The insert 312 in one embodiment is integrally formed of silicone via an injection molded process. Silicone provides a suitable material for the insert in that it is sufficiently strong, compliant, non-shedding, stable in the presence of a cleansing solution, and provides a suitable surface for retention of the cleansing solution. Of course, other suitable processes and materials can be used to form the insert. In one embodiment, the fingers and/or wipers can be formed separately from the base and later attached thereto to define the insert.

A cleansing solution 313, such as a suitable disinfectant, is included with the insert 312 within the cavity of the scrub brush holder 311 and includes a surface tension that enables it to adhere to the fingers 317 and wipers 318 of the insert 312. So configured, the cleansing solution 313 coats the surfaces of the insert 312 and is in place when the scrub brush 310 is used to clean a portion of a medical device or other component, as has been described.

In the current embodiment, the fingers 317 are centered about a longitudinal axis of the insert 312 in a square three-by-three grid, while four pairs of wipers 318 are equidistantly spaced about the inner circumference of the insert wall 316. So positioned, each wiper 318 extends into a space adjacent the fingers 317 proximate thereto. This in turn enables the wipers 318 to compliantly engage the exterior portion of a connector or other device inserted into the cavity of the holder 311 for cleansing, while the fingers 317 compliantly engage and cleanse an interior portion of the connector/device. In other words, the insert fingers 317 are biased against inside surfaces of the connector to effect a wiping action when the scrub brush is rotated relative to the connector, while the wipers 318 are biased against the exterior surfaces of the connector to effect an external wiping action, which enables the cleansing solution to contact the surfaces and kill any bacteria/microbes thereon.

In the present embodiment, the insert 312 is sized to permit, for example, a female luer connector to be inserted a sufficient distance into the cavity of the scrub brush holder 311 to engage the fingers 317 and wipers 318 of the insert and provide for cleansing of the inside and outside surfaces thereof, including any threads of the luer connector, when the scrub brush and luer connector are rotated relative to one another.

As illustrated in FIGS. 28 and 29, each finger 317 includes a circular cross-section and extends from the insert base 315 to a top plane of the insert 312. Each wiper 318 includes a rectangular cross-section and also extends from the base 315 to the top plane of the insert 312.

FIGS. 30 and 31 depict the insert 312 according to one embodiment, wherein the four equidistantly placed pairs of wipers 318 are each replaced with a single wiper 318. In addition, each wiper 318 in FIG. 30 defines a stepped configuration, including a thick section 319 adjacent the insert wall 316, and a thin section 320 radially inward of the thick section. So configured, each wiper 318 extends proximate to a respective one of the fingers 317. It is appreciated that the wipers can be offset or rotated in position about the circumference of the wall of the insert.

From the above, it is appreciated that the number, shape, and size of the wipers and fingers can vary from what is shown and described herein to suit a particular need or application. FIGS. 32-38 give non-limiting examples of this. For example, FIGS. 32 and 33 show that one or more of the fingers 317 in one embodiment can define a stepped profile with a circular cross-section, wherein approximately half of the finger is of a relatively larger diameter than the remaining half. FIG. 34 shows a variation of the above stepped profile, wherein approximately three-fourths of the length of the finger 317 is of a relatively larger diameter than the remaining one-quarter of the finger length.

FIGS. 35-38 show additional and non-limiting variations of possible finger configurations. In particular, FIGS. 35 and 36 show that the finger 317 in one embodiment defines a uniform profile with a square cross-section, while FIGS. 37 and 38 depict fingers 317 including round and triangular cross-sections, respectively. Other cross-sectional shapes are also possible.

It is noted that the scrub brush can be configured in any one of a variety of sizes. In one embodiment, for example, the scrub brush can include a holder sized to contain up to about 0.75 cc of a cleansing solution detailed above, for instance, such that at least one-half of the solution adheres to the surfaces of the insert. In another embodiment, the wipers can extend radially outward or inward from a relatively smaller diameter wall than the wall 316 (FIGS. 28, 30) or other suitable structure of the cleansing insert. In yet another embodiment, the wipers can extend laterally with respect to the longitudinal axis of the insert, instead of vertically as depicted in the accompanying figures. These and other modifications are therefore contemplated.

It should be further appreciated that the scrub brush described herein can be modified to cleanse other devices and components not explicitly discussed herein, such as ear/nose probes, ultrasound probes, and non-medical devices where simple cleansing is desired.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A scrubbing device for cleansing a portion of a device, comprising:
    a holder;
    a cleansing insert included with the holder, the cleansing insert including:
        a base portion;
        an outer wall extending from the base portion to define a chamber; and
        a plurality of fingers extending from the base portion into the chamber; and
    a cleansing solution included with the cleansing insert to enable surfaces of the device portion to be cleansed by the fingers when the device portion is engaged by the cleansing insert.

2. The scrubbing device as defined in claim 1, wherein the cleansing insert further comprises a plurality of wipers.

3. The scrubbing device as defined in claim 2, wherein the wipers extend radially inward from the outer wall.

4. The scrubbing device as defined in claim 3, wherein at least one of the plurality of wipers and the plurality of fingers defines a stepped profile.

5. The scrubbing device as defined in claim 3, wherein the wipers are spaced equidistantly about a circumference of the outer wall.

6. The scrubbing device as defined in claim 1, wherein the cleansing insert includes silicone.

7. The scrubbing device as defined in claim 1, wherein the cleansing insert is formed via injection molding.

8. The scrubbing device as defined in claim 7, wherein the cleansing insert includes silicone foam.

9. The scrubbing device as defined in claim 1, wherein the holder defines a cavity in which the cleansing insert is disposed, wherein a plurality of wipers included with the cleansing insert engages an exterior surface of the device, and wherein the fingers engage an interior of the device when the portion of the device is received in the cavity and the cleansing insert is moved relative to the portion to enable cleansing thereof by the cleansing solution included with the fingers and the wipers.

10. A method for cleansing a portion of a device, the method comprising:

providing a scrubbing device including a holder defining a cavity and an insert disposed within the cavity, the insert including a base having an outer wall and a plurality of centrally disposed fingers extending from a side of the base, the outer wall including a plurality of wipers extending radially inward, the fingers and wipers further including a cleansing solution;

inserting the portion of the device into the cavity; and rotating the scrubbing device with respect to the portion of the device received within the cavity such that at least one of the fingers and wipers engages and cleanses a surface of the portion of the device with the cleansing solution.

11. The method for cleansing as defined in claim 10, wherein rotating the scrubbing device further comprises:

rotating the scrubbing device with respect to the portion of the device received within the cavity such that the fingers engage an interior surface of the device and the wipers engage an exterior surface of the device.

12. The method for cleansing as defined in claim 10, wherein the device is a medical device, wherein the fingers and wipers are compliant, and wherein inserting the portion of the medical device into the cavity further comprises:

inserting the portion of the medical device into the cavity such that a compressive engagement of the fingers or the wipers with the portion is achieved.

13. The method for cleansing as defined in claim 10, wherein rotating the holder further comprises:

rotating the holder a predetermined number of times so as to remove a biofilm from the portion of the device with the fingers and wipers of the scrubbing device.

14. A scrubbing device for cleansing a portion of a medical device, comprising:

a holder defining a cavity for receipt of the portion of the medical device;

a cleansing insert disposed in the cavity of the holder, the cleansing insert including:

a base portion;

a plurality of fingers extending from the base portion; and a plurality of wipers extending radially inward toward the plurality of fingers into the cavity; and a cleansing solution included with cleansing insert to cleanse surfaces of the medical device portion that are engaged by at least one of the plurality of fingers and the plurality of wipers.

15. The scrubbing device as defined in claim 14, wherein the insert further includes an outer wall extending from the base, the wipers extending radially inward from the wall, the wall defining a chamber in which the fingers are disposed.

16. The scrubbing device as defined in claim 15, wherein the fingers and the wipers are compliant so as to compress against the surfaces of the medical device when the portion of the medical device is received in the cavity of the holder.

17. The scrubbing device as defined in claim 16, wherein the cleansing insert is injection molded and includes silicone, and wherein the fingers are arranged in a three-by-three grid.

18. The scrubbing device as defined in claim 14, wherein the fingers include a round cross-sectional shape and wherein at least one of the plurality of fingers and the plurality of wipers includes a stepped profile.

19. The scrubbing device as defined in claim 14, wherein the medical device is a connector, wherein the fingers are configured to engage an interior surface of the connector, and wherein the wipers are configured to engage an exterior surface of the connector.

20. The scrubbing device as defined in claim 14, wherein the wipers are arranged in pairs, the pairs being equidistantly spaced about a circumference of the outer wall.

21. The scrubbing device as defined in claim 14, wherein the medical device is selected from the group consisting of: a catheter, an ear probe, a nose probe, and an ultrasound probe.

22. A scrubbing device for cleansing a portion of a medical device, comprising:

a holder defining a cavity for receipt of the portion of the medical device;

an injection molded cleansing insert including silicone, the cleansing insert disposed in the cavity of the holder and including:

a base portion;

an outer wall extending from the base and defining a chamber;

a plurality of fingers extending from the base portion into the chamber; and a plurality of wipers extending from the outer wall radially inward into the chamber; and a cleansing solution included with cleansing insert to cleanse surfaces of the medical device portion that are engaged by at least one of the plurality of fingers and the plurality of wipers.

* * * * *